(12) United States Patent
Clayton et al.

(10) Patent No.: US 6,434,507 B1
(45) Date of Patent: Aug. 13, 2002

(54) MEDICAL INSTRUMENT AND METHOD FOR USE WITH COMPUTER-ASSISTED IMAGE GUIDED SURGERY

(75) Inventors: John B. Clayton, Superior; Mark W. Hunter, Broomfield, both of CO (US); David Lightman, Plantation; Thomas J. Mickel, Jupiter, both of FL (US)

(73) Assignee: Surgical Navigation Technologies, Inc., Louisville, CO (US)

( * ) Notice: Subject to any disclaimer, the term of this patent is extended or adjusted under 35 U.S.C. 154(b) by 0 days.

(21) Appl. No.: 09/598,975

(22) Filed: Jun. 21, 2000

Related U.S. Application Data

(63) Continuation of application No. 09/063,410, filed on Apr. 21, 1998, now abandoned.
(60) Provisional application No. 60/057,670, filed on Sep. 5, 1997.

(51) Int. Cl.[7] .................................................. A61B 5/00
(52) U.S. Cl. ........................ 702/152; 702/150; 600/117; 600/104
(58) Field of Search ................................. 702/150, 152; 600/117, 104, 411, 414, 424; 382/128, 130, 131

(56) References Cited

U.S. PATENT DOCUMENTS

| | | |
|---|---|---|
| 3,963,028 A | 6/1976 | Cooley et al. |
| 4,182,312 A | 1/1980 | Mushabac |
| 4,407,298 A | 10/1983 | Lentz et al. |
| 4,431,005 A | 2/1984 | McCormick ............... 128/656 |
| 4,465,069 A * | 8/1984 | Barbier et al. ........... 128/303 B |
| 4,733,661 A | 3/1988 | Palestrant |
| 4,733,662 A | 3/1988 | DeSatnick et al. |
| 4,742,815 A | 5/1988 | Ninan et al. |
| 4,791,934 A | 12/1988 | Brunnett |
| 4,805,615 A | 2/1989 | Carol |
| 4,835,710 A | 5/1989 | Schnelle et al. |
| 4,841,967 A | 6/1989 | Chang et al. |
| 4,875,478 A | 10/1989 | Chen |
| 4,943,296 A | 7/1990 | Funakubo et al. |
| 4,955,891 A | 9/1990 | Carol |
| 5,017,139 A | 5/1991 | Mushabac |
| 5,047,036 A | 9/1991 | Koutrouvells |
| 5,050,608 A | 9/1991 | Watanabe et al. |
| 5,078,140 A | 1/1992 | Kwoh |

(List continued on next page.)

FOREIGN PATENT DOCUMENTS

| | | |
|---|---|---|
| EP | 0 359 773 | 5/1988 |
| EP | 0 326 768 | 12/1988 |
| EP | 0 469 966 | 7/1991 |
| WO | WO 88/09151 | 12/1988 |
| WO | WO 97/40764 | 11/1997 |

OTHER PUBLICATIONS

W. Krybus, A. Knepper, L. Adams, R. Rüger, D. Meyer-Ebrecht, *Navigation Support for Surgery by Means of Optical Position Detection*, pp. 362–366.

K. Obergfell and W. J. Book, *End–Point Position Measurements of Long–Reach flexible Manipulators*.

*Primary Examiner*—Marc S. Hoff
*Assistant Examiner*—Carol S. Tsai
(74) *Attorney, Agent, or Firm*—Harness, Dickey & Pierce, P.L.C.

(57) ABSTRACT

An apparatus is disclosed for use with a surgical navigation system. The apparatus comprises a tool body and tool attachment onto which emitters are fixedly mounted. At least one tool tip is removably coupled with the tool body. An electrical sensor is positioned to be operated when the tool tip is changed either by coupling the tip to or removing the tip from the tool body. A controller responsive to the operation of switch detects when the tip has been changed. An alarm responsive to the controller indicates that the tool tip has been removed or changed so that the tip can be recalibrated relative to a known position in the surgical navigation system.

51 Claims, 6 Drawing Sheets

U.S. PATENT DOCUMENTS

| | | | |
|---|---|---|---|
| 5,080,662 A | 1/1992 | Paul | |
| 5,086,401 A | 2/1992 | Glassman et al. | |
| 5,142,930 A | 9/1992 | Allen et al. | |
| 5,284,154 A | * 2/1994 | Raymond et al. | 128/741 |
| 5,299,288 A | 3/1994 | Glassman et al. | |
| 5,305,203 A | 4/1994 | Raab | |
| 5,186,174 A | 2/1993 | Schlöndorff et al. | |
| 5,197,476 A | 3/1993 | Nowacki et al. | |
| 5,198,877 A | 3/1993 | Schulz | |
| 5,211,175 A | 5/1993 | Ishiguro et al. | 128/662.06 |
| 5,224,049 A | 6/1993 | Mushabac | |
| 5,230,623 A | 7/1993 | Guthrie et al. | |
| 5,251,127 A | 10/1993 | Raab | |
| 5,257,998 A | 11/1993 | Ota et al. | |
| 5,309,913 A | 5/1994 | Kormos et al. | |
| 5,325,873 A | 7/1994 | Hirschi et al. | 128/899 |
| 5,357,953 A | 10/1994 | Merrick et al. | |
| 5,383,454 A | 1/1995 | Bucholz | |
| 5,494,034 A | 2/1996 | Schlöndorff et al. | |
| 5,517,990 A | 5/1996 | Kalfas et al. | |
| 5,578,052 A | 11/1996 | Koros et al. | 606/174 |
| 5,617,857 A | * 4/1997 | Chader et al. | 128/653.1 |
| 5,748,767 A | 5/1998 | Raab | |
| 5,806,518 A | * 9/1998 | Mittelstadt | 128/653.1 |
| 5,814,038 A | * 9/1998 | Jensen et al. | 606/1 |
| 5,848,967 A | 12/1998 | Cosman | |
| 5,851,183 A | * 12/1998 | Bucholz | 600/425 |
| 5,855,583 A | * 1/1999 | Wang et al. | 606/139 |
| 5,891,034 A | * 4/1999 | Bucholz | 600/426 |
| 5,891,158 A | * 4/1999 | Manwaring et al. | 606/130 |
| 5,954,648 A | * 9/1999 | Van Der Brug | 600/411 |
| 5,980,535 A | * 11/1999 | Barnett et al. | 606/130 |
| 6,006,126 A | * 12/1999 | Cosman | 600/426 |
| 6,007,550 A | * 12/1999 | Wang et al. | 606/139 |
| 6,020,875 A | * 2/2000 | Moore et al. | 345/156 |
| 6,076,008 A | * 6/2000 | Bucholz | 600/427 |
| 6,190,395 B1 | * 2/2001 | Williams | 606/130 |
| 2001/0029333 A1 | * 10/2001 | Shahidi | 600/129 |

* cited by examiner

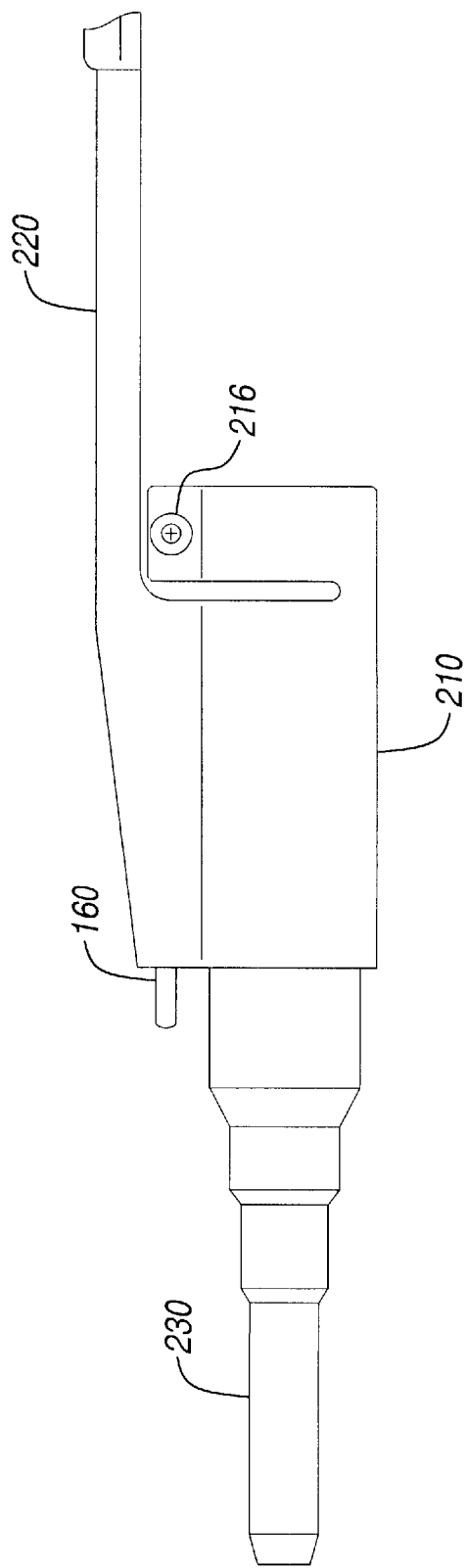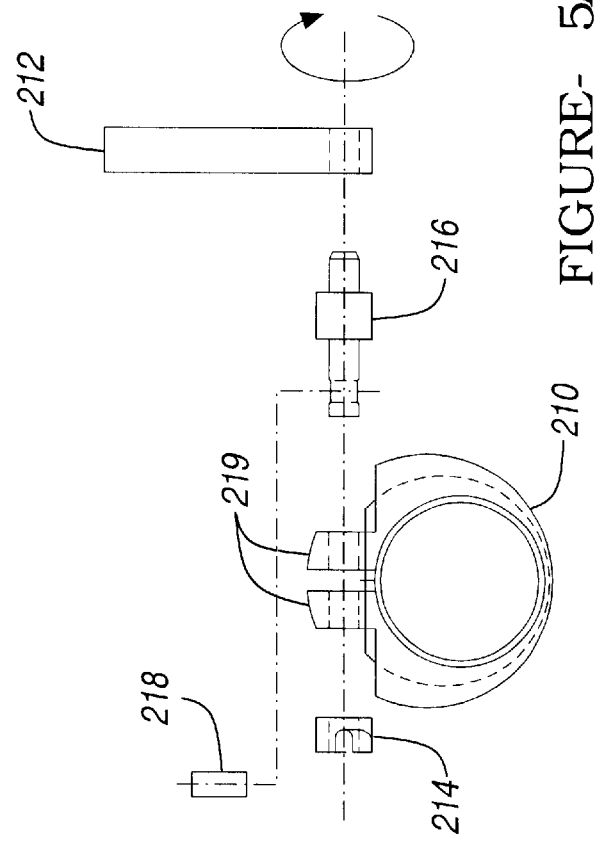

MEDICAL INSTRUMENT AND METHOD FOR USE WITH COMPUTER-ASSISTED IMAGE GUIDED SURGERY

This is a continuation of application Ser. No. 09/063,410, filed Apr. 21, 1998, now abandoned which is incorporated herein by reference.

The present invention claims rights under 35 U.S.C. §119 on Provisional Application No. 60/057,670, filed on Sep. 5, 1997, and entitled "Improved Medical Instrument and Method for use with Computer-Assisted Image Guided Surgery."

FIELD OF THE INVENTION

The present invention relates generally to systems which use and generate images during medical and surgical procedures, which images assist in executing the procedures and indicate the relative position of various body parts and instruments. In particular the invention relates to a system for generating images during medical and surgical procedures that indicate a change in the condition or configuration of a medical instrument being used, wherein the system provides a positive indication of the position of a removable or interchangeable portion of the instrument.

BACKGROUND OF THE INVENTION

A number of different types of surgical navigation systems have been described that include indications of the positions of medical instruments used in medical or surgical procedures. For example, U.S. Pat. No. 5,383,454 to Bucholz; PCT Application No. PCT/US94/04530 (Publication No. WO 94/24933) to Bucholz; and PCT Application No. PCT/US95/12894 (Publication No. WO 96/11624) to Bucholz et al., the entire disclosures of which are incorporated herein by reference, disclose systems for use during a medical or surgical procedure using scans generated by a scanner prior to the procedure. Surgical navigation systems typically include tracking means such as for example an LED array on the body part, emitters on the medical instruments, a digitizer to track the positions of the body part and the instruments, and a display for the position of an instrument used in a medical procedure relative to a body part. Although these types of systems are effective, further improvements are now possible for tracking the change of instrument configuration during surgery. For example, when using a high speed drill or other tool in surgery, typically this instrument uses an interchangeable attachment that allows for the use of different tool tips, such as for example different length drill bits and burrs. A simple, reliable way is desirable for the change in these tips to be indicated by the surgical navigation system to require the user or surgeon to properly recalibrate or reregister the position of the end of the instrument tip relative to some known point.

Additionally, if the emitter on an attachment end is not stably positioned, the navigation system may lose information on the location of the attachment and tool tip. The advantage of a stable geometry is that the position of the working portion of the instrument with respect to the LED array cannot be changed by the user. In prior art systems the LED array is generally attached to the surgical drill. If the user changes the attachment or the attachment is unscrewed slightly from the drill then location information may be lost. One example of this is an angled attachment that is screwed onto an image guided drill. The tip of this attachment can describe an arc as it is unscrewed from the drill because the LED array is not co-axial with the working portion of the attachment and location information may be lost; however, if the LED array is more permanently connected, as with the present invention, for example such as to a tool attachment, then the relationship between the LED array and working portion of the instrument is generally constant regardless of whether the attachment is loosened or not.

Other attachments to an instrument, such as for example a bent end craniotome, may favor a rotatable connection of an emitter to the attachment to allow the user to point the tip of an attachment (which may be at an angle to the instrument shaft) in the desired direction and still have a continued line of sight emission to the digitizer camera while rotating the attachment relative to the navigation system. Given the above information, it is sometimes advantageous for a surgeon to be able to rotate a surgical drill attachment in order to position the attachment in a specific way. For example, a portion of a surgical burr may be covered by a cowl (connected to the attachment) so that the burr can cut in only one direction. In order to position the cutting portion of the burr, the surgeon may have to rotate the attachment, and the LED array may be forced to point away from the digitizer camera when the attachment is rotated. However, if the attachment and LED array are connected so that they can rotate independently, as in for example, an alternative embodiment of the invention described herein, then the LED array can be directed toward the camera and the attachment still rotated in the desired direction. This concept is feasible in situations where the LED array and working portion of the attachment are coaxial (e.g. "straight attachments").

In light of the foregoing, there is a need in the art for an improved surgical navigation system and method for indicating a change in instrument configuration that provides a means to reliably calibrate the location of an instrument with interchangeable tips that does not significantly affect the accuracy of the localization of the system.

SUMMARY OF THE INVENTION

Accordingly, the present invention is directed to a medical instrument with a tracking means able to locate the position of the instrument in a surgical field, such as electrically energizeable emitters, reflective markers, magnetic sensors or other locating means, for use with a surgical navigation system and method that substantially improves the task of positively indicating to the surgical navigation system when an instrument attachment has been changed or removed and positively providing a link between the position of this changeable instrument attachment and the image provided by the surgical navigation system.

To achieve these objects and other advantages and in accordance with the purpose of the invention, as embodied and broadly described herein, the invention in one embodiment is an apparatus for use with a surgical navigation system and comprises a tool body, an instrument attachment onto which a tracking means such as, for example, emitters are fixedly mounted, at least one tool tip for removably coupling with the instrument attachment, a sensor positioned to be automatically operated when the tool tip is changed either by coupling the tip to or removing the tip from the instrument attachment, a controller responsive to the operation of the switch to detect when the tip has been changed, and an alarm responsive to the controller for indicating that the tool tip has been removed or changed so that the tip can be relocated relative to a known position in the surgical navigation system.

In another aspect, the sensor operated when the tool tip is changed is an electrical switch, such as for example a microswitch.

In another aspect, the surgical navigation system disables the tool when the electrical switch has been operated until the tool tip position is calibrated relative to a known position in the surgical navigation system. In this manner, the navigation system indicates the accurate tool tip location during the operation of the tool.

In another aspect, the electrical switch operates in response to the insertion or release of a tool tip to an attachment or to the tool body such as, for example, by pressing an attachment ring against the switch and a mechanical release, such as for example a chuck, to simultaneously activate the switch when releasing or attaching a tool tip. In this manner, the navigation system need not rely on the operator to know or remember to indicate a change in tool tips. The instrument automatically indicates this change or removal in tool tip to allow the navigation system to properly respond.

In another aspect, the surgical navigation system communicates to the user, for example, by means of a flashing LED on the tool tip instrument attachment or tool body, to positively indicate the attachment and relocation of the tool tip. In this manner, the user knows, by positive indication back from the navigation system, that it can proceed.

In another aspect, emitters are fixedly attached to the instrument attachment. This is accomplished, for example, by press fitting a cage that holds the emitters in place onto the instrument attachment. By fixedly attaching the emitter to the instrument attachment, the user or operator reduces the risk that loss in positioning will occur during the procedure due to an emitter erroneously changing its location relative to the instrument attachment or tool tip.

In another aspect, an emitter is rotatably connected to the instrument attachment. This is accomplished, for example, by providing a groove inside the end of a cage at the position where the tool attachment connects to the cage and disposing bearings or other rotatable devices in the groove to facilitate free rotation of the tool attachment and tool tip. By rotatably connecting the instrument attachment to the cage, the operator can more readily achieve a line of sight indication from the emitter, fixed to the cage, back to the digitizer of the navigation system which is less dependent on the orientation of the instrument attachment and tool tip.

In another aspect, the emitters attached to the tool are light emitting diodes ("LEDs").

In another aspect, the controller is a suitably programmed personal computer ("PC") or appropriate computer device.

In another aspect, the alarm is a visual designation or indicator on a PC monitor display or audible indication.

In another aspect, calibration of the tool tip location is accomplished by the user returning the tool tip to a datum, benchmark or known position for calibrating the location of the tip in three dimensional space. This simple method of calibration avoids the necessity of reentering data corresponding to a change in tool tips to accurately locate the tool tip.

In another aspect, calibration is accomplished, for example, by fiber optic reading of a bar code on the tool tip. In this manner, the operator is further allowed easy entry of the accurate calibration and configuration of the tool tip without the need for data entry.

In another aspect, calibration is accomplished by selection of options from a menu displayed by the navigation system. This aspect of the apparatus and method provides further simple and easy access to enter an accurate configuration and location without complicated data entry.

In addition, the invention in one embodiment comprises a surgical navigation system including: a controller; a tool and tool tip; a means for coupling a tool tip; a means for detecting the coupling and uncoupling of the tool tip; a means for delivering an alarm when the tool tip is changed by uncoupling or coupling; and a means for recalibrating or relocating the tool tip relative to a known point in the surgical navigation system.

In addition, the invention further comprises a method for monitoring the location of an instrument, an instrument attachment, and tool tip used in a surgical navigation system comprising the steps of: coupling an instrument attachment having at least one emitter to a tool; automatically tripping a switch in response to the coupling step occurring; delivering an alarm when the tool tip is coupled and uncoupled; and calibrating the tool tip relative to a known position in the surgical navigation system.

The objects of the invention are to provide a user, such as a surgeon, with the system and method to track an instrument used in conjunction with a surgical navigation system in such a manner that changing the tool tip or attachment of the instrument does not substantially affect the accuracy of the localization of the system.

It is a further object of this invention to provide a system and method to simply and yet positively indicate to the user a change in configuration, such as the removal or change of an instrument attachment or tool tip (e.g. drill bit, burr, probe, catheter, tube, needle, delivery system).

It is a further object of this invention to provide a system and method to reliably deactivate or disable an instrument being used with a surgical navigation system, after the tool tip has been changed, until the relative location or positioning of the instrument, its attachment, and tool tip is recalibrated or verified.

It is a further object of this invention to provide a system and method with a stable geometry of an emitter and instrument attachments of varying configurations to provide an accurate indication of the location of the attachment's location relative to a known point or points in the navigation system, for numerous alternative shapes of the instrument attachment.

It is a further object of this invention to provide a system or method with a variable or rotatable geometry between emitter and instrument attachments of varying configurations to provide an accurate indication of the location of the attachment's location and tip end relative to a known point or points in the navigation system, for varying shapes or orientations of the instrument attachment.

It is a further object of this invention to provide a system or method for positively locking the instrument attachment to the instrument to reduce loosening during a procedure.

It is another object of this invention to provide a system and method for positively generating a display of the position of an instrument attachment or tool tip.

It is a further object of this invention to provide an apparatus and method for bi-directional communication between the surgical navigation system and the instrument attachment to allow control of the instrument, instrument attachment or tool tip by the surgical navigation system or to indicate to the user that the attachment has been properly installed and its position calibrated and is otherwise ready for use in the procedure in concert with the remainder of the surgical navigation system.

Additional objects and advantages of the invention will be set forth in part in the description which follows, and in part will be obvious from the description, or may be learned by practice of the invention. The objects and advantages of the invention in its various embodiments will be realized and attained by means of the elements and combinations particularly pointed out in this description.

It is to be understood that both the foregoing general description and the following detailed description are exemplary and explanatory only and are not restrictive of the invention.

BRIEF DESCRIPTION OF THE DRAWINGS

The accompanying drawings, which are incorporated in and constitute a part of this specification, illustrate one embodiment of the invention and together with the description, serve to explain the principles of the invention.

FIG. 5 is a side view of another embodiment of a tool, cage, and tool attachment according to the invention adapted for an alternative locking mechanism.

FIG. 5A is an exploded front view of the cage of FIG. 5 and associated locking mechanism.

DESCRIPTION OF THE PREFERRED EMBODIMENT

Reference will now be made in detail to the present preferred embodiment of the invention, an example of which is illustrated in the accompanying drawings. Wherever possible, the same reference numbers will be used throughout the drawings to refer to the same or like parts. The following example is intended to be purely exemplary of the invention.

Figure 1:
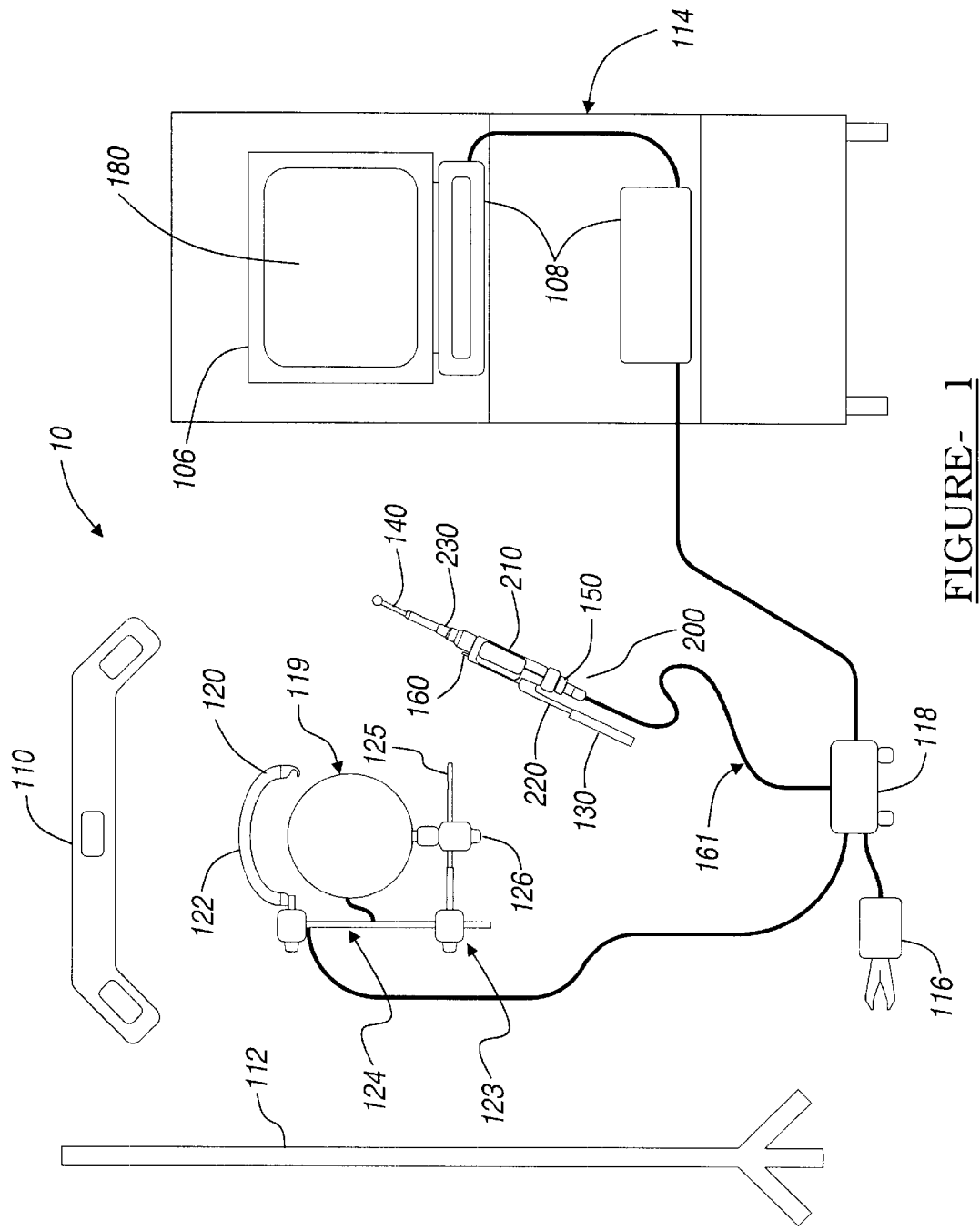
FIG. 1 is a schematic diagram of one preferred embodiment of a cranial surgical navigation system with a medical instrument according to the invention.

As generally described in PCT/US95/12894, the entire disclosure of which is incorporated herein by reference, a typical surgical navigation system is shown in FIG. 1. A computer assisted image guided surgery system, indicated generally at 10, generates an image for display on a monitor 106 representing the position of one or more body elements, such as a cranium represented by circle 119 fixedly held in a well-known clamping device such as a Mayfield clamp assembly 123 indicated generally at 124, 125, and 126. A reference arc 120 bearing tracking means such as for example LED emitters 122 is mounted to the Mayfield clamp 123. The image is generated from an image data set, usually generated preoperatively by a CAT scanner for example, which image has reference points for at least one body element, such as cranium 119. The reference points of the particular body element have a fixed spatial relation to the particular body element. The system includes an apparatus such as a digitizer or other Position Sensing Unit (PSU), such as for example sensor array 110 on support 112 for identifying, during the procedure, the relative position of each of the reference points to be displayed by tracking the position of emitters 122 on arc 120. The system also includes a processor 114 such as a PC or other suitable workstation processor associated with controller 108 for modifying the image data set according to the identified relative position of each of the reference points during the procedure, as identified by digitizer 110. The processor 114 can then, for example, generate a displaced image data set representing the position of the body elements during the procedure for display on monitor 106. An instrument 200 of the present invention, as further described in detail below, used during the procedure, may be included in the system, which is positioned relative to a body part and similarly tracked by sensor array 110. In summary, the operation of a surgical navigating system is well known in the art and need not further be described here.

Figure 2:
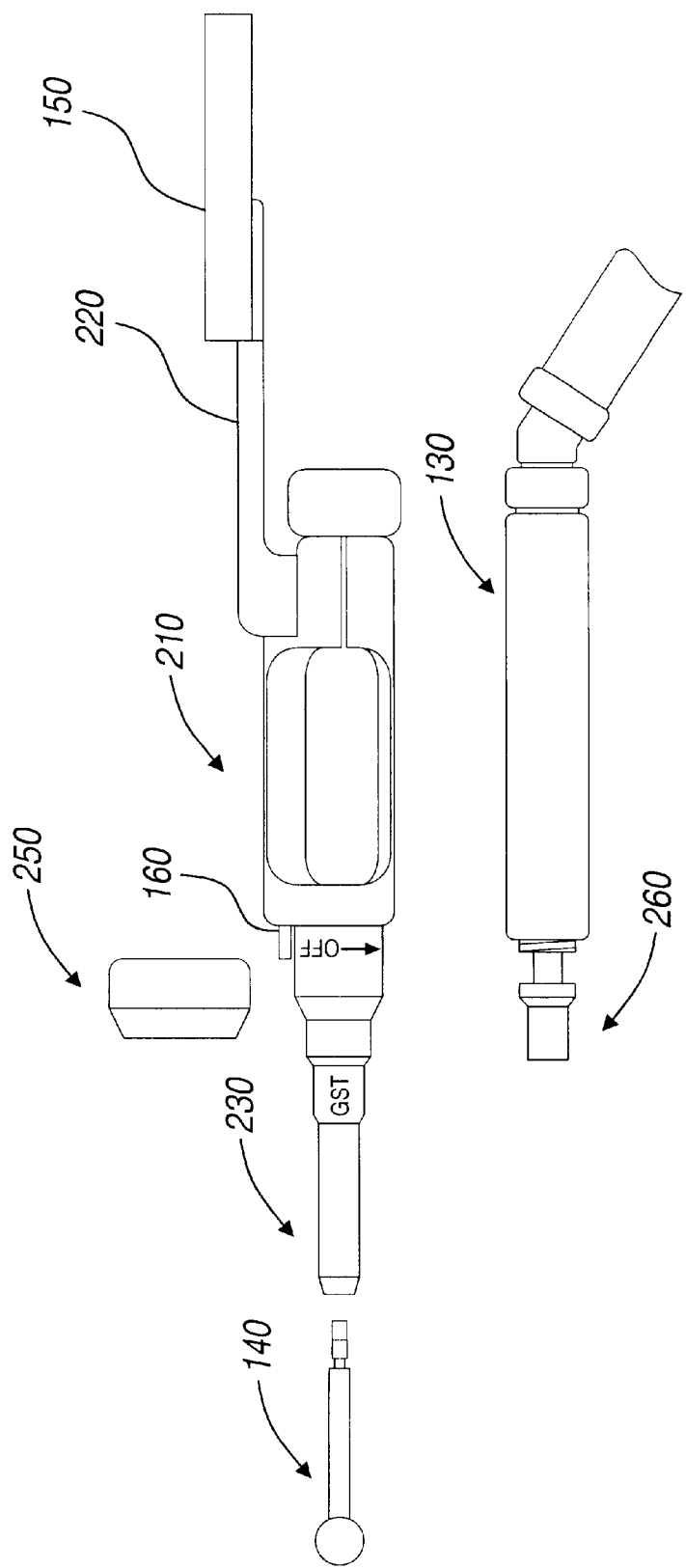
FIG. 2 is a side view of one preferred embodiment of a medical instrument with a tool, cage, tool attachment and interchangeable tip end according to the invention.
Figure 3:
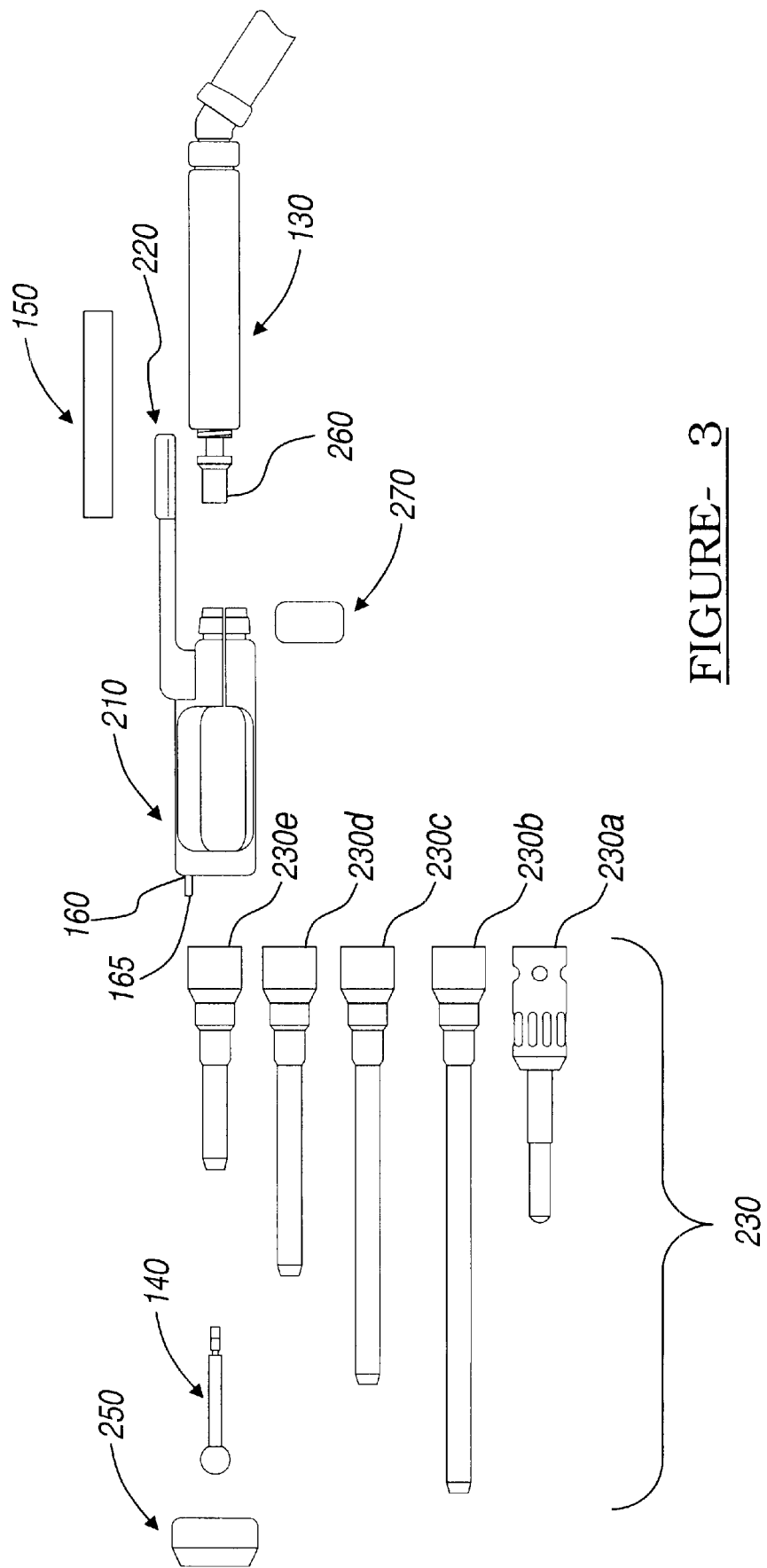
FIG. 3 is an exploded side view of one preferred embodiment of a tool, cage, alternative tool attachments, tool tip, attachment ring, and thumb ring.

In accordance with the preferred embodiment of the present invention, with further reference to FIGS. 1, 2 and 3, a medical instrument 200 is provided for use with the surgical navigating system. This instrument 200 may be a drill, probe, catheter, biopsy guide, or other appropriate medical instrument well known in the art for carrying out desired procedures. Instrument 200 includes a tool body 130, a cage 210 with an arm 220 on which emitters 150 are fixedly mounted, a tool attachment 230 and at least one tool tip 140 for removably a coupling to said tool body 130 through tool attachment 230 to form medical instrument 200. Electrical switch 160 or other suitable sensor is automatically physically operated when tool tip 140 is physically changed by either coupling to or removal from the tool body 130 of instrument attachment 230. A controller 108 such as for example that associated with PC or other workstation 114 is operably connected to the switch 160, such as through cable 161 through junction box 118 and is responsive to the operation of switch 160. An alarm or other indication of some type, such as a message or display 180 on monitor 106, is generated by controller 108 indicating to the user such as a surgeon that tool tip 140 of tool 200 had been changed.

As embodied herein, arm 220 has emitters 150 either fixedly or rotatably mounted for providing a positive emission to locate the tool tip 140 by camera array 110 or other emitter receptor. The emitter 150 is preferably a light emitting diode ("LED"), but can be any other energy radiating device or tracking means known in the art capable of being tracked by a corresponding detector array.

Additionally, as embodied herein, a coupling for the tool tip 140 to the tool body 130 may include any of a number of mechanical arrangements, including ring mounts, chucks or other mechanical means, Switch 160, the means for detecting the coupling or uncoupling of the tool tip 140, is preferably a microswitch but can be embodied by any suitable electrical or electromechanical device or other sensing device capable of providing a signal in response to attachment or detachment at a particular point on the tool body 130 or tool tip 140. As depicted, for example, in FIG. 2, the tool body 130 is inserted into cage 210 and locked in place by ring 270, Tool tip 140 is then inserted into attachment 230. To load tool tip 140, attachment ring 250 slides axially over attachment 230 and body of ring 250 depresses switch 160 while prongs on ring 250 depress chuck 260. Tool tip 140 is then attached to tool body 130 through chuck 260. FIG. 3 also depicts an expanded perspective of this preferred embodiment, indicating alternative configurations of attachment 230 (230a, 230b, 230c, 230d and 230e) apart from cage 210 such that the activating pin 165 for switch 160 is discernable and thumb ring 270 for connecting tool body 130 and cage 210 is also depicted.

Figure 4:
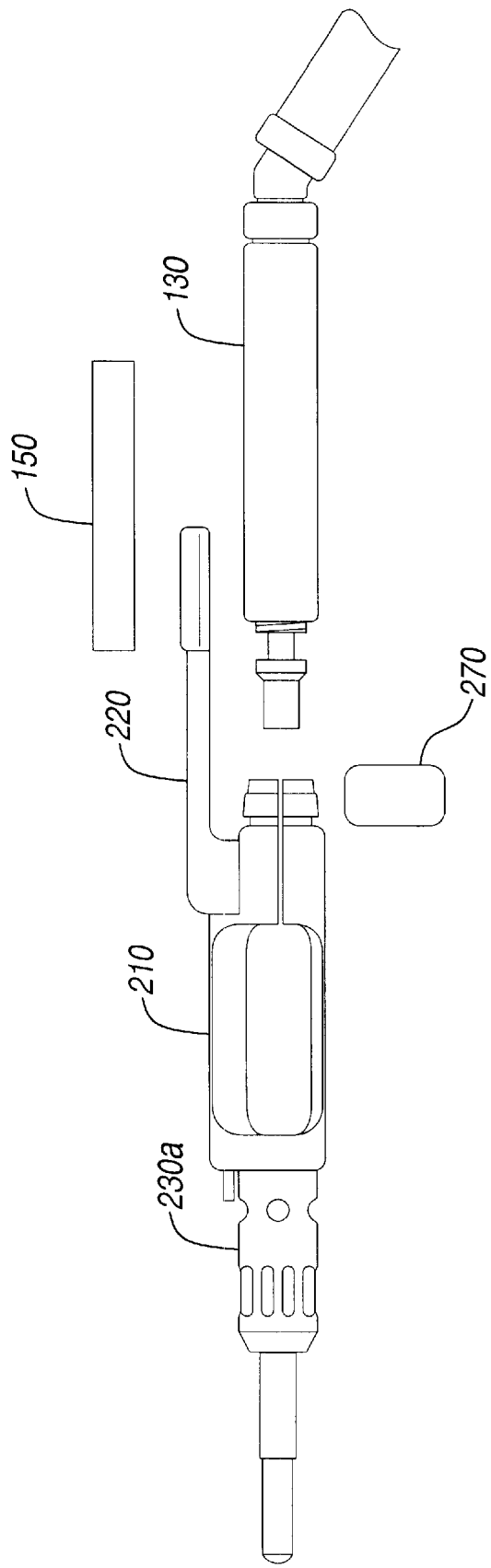
FIG. 4 is a side view of another embodiment of a tool, cage, and tool attachment according to the invention.

FIG. 4 depicts an alternative embodiment of tool 200 wherein attachment 230a, such as, for example a craniotome, is rotatably attached to cage 210 by resting on bearings (not shown) in a groove formed on cage 210 at the interface of cage 210 and attachment 230a.

FIGS. 5 and 5A depict an alternative embodiment of cage 210 wherein a locking mechanism is provided for positively locking tool body 130 in place. In this configuration, tool body 130 is inserted into cage 210 and lever 212 is rotated. The rotation of lever 212 is transmitted to follower 218 by shaft 216, forcing follower 218 to follow the profile of cam 214 and close the gap between ears 219 of cage 210. Closing the gap effectively reduces the circumference of the inner diameter of the cage 210 thereby clamping cage 210 onto tool body 130.

The alarm is preferably an audible indication or video display 180 on a monitor 106, or could be any suitable speaker, sound or light emitting apparatus. Alternatively, an electric pulse may be delivered to the operator by means of a vibrating or pulsating device, such as commonly available for pagers and other systems.

Further in accordance with FIGS. 1–4, a tool or surgical instrument 130 such as a drill, cauterizer, fiber optic scope, biopsy guide frame, probe, or other delivery system, with tip 140, such as a drill bit, burr, needle, heating element, knife end, tube or other attachment of varying shapes, sizes, lengths and configurations is provided. Arm 220 has LEDs 150 press fit, screwed and/or glued to it to achieve a stable geometry between the emitters 150 and tool tip 140. In an alternative embodiment LEDs 150 may be rotatably mounted to cage 210 to allow alternate orientations of the tool body 130 and tool tip 140 without loss of line of sight indication by means of the emitter 150 to array 110. Alternatively, the location of this tool tip may be accomplished by a signal generated by an electrical switch.

Additionally, microswitch 160 can be integrated on cage 210. The microswitch 160 is positioned so that it must be depressed by attachment ring 250 any time that the tool tip 140 is changed.

The wires for the switch 160 are run directly to the controller 108 by means of the junction or breakout box 118 to provide communication of any changes in the status of switch 160, which can be read by controller 108 in routine fashion. Alternatively, if a wireless probe or other instrument is used, such as one with passive reflective surfaces in place of LED emitters, any suitable form of communication known in the art can be used.

Figure 6:
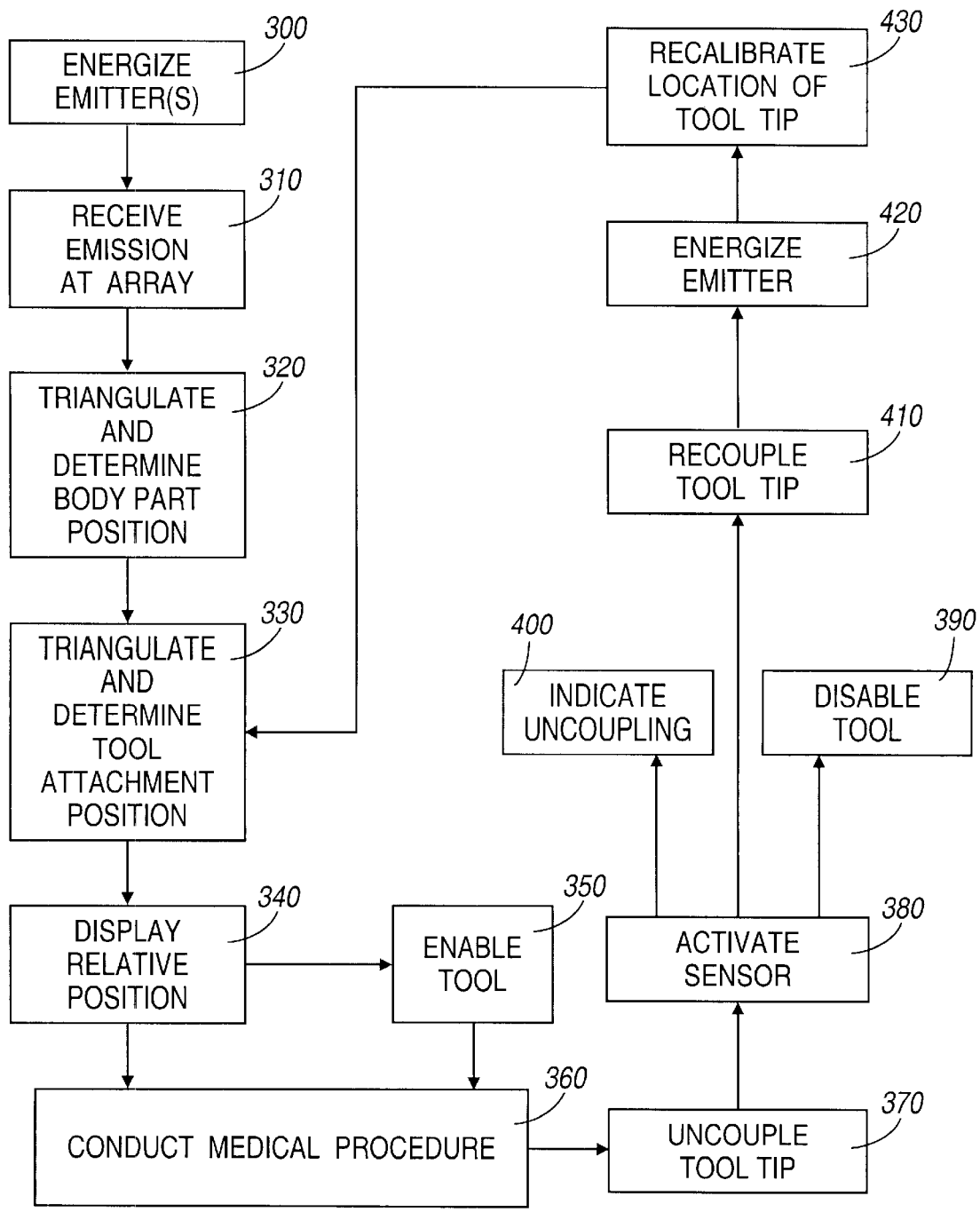
FIG. 6 is a flowchart of one preferred embodiment of a method to practice the invention in a medical procedure employing a surgical navigation system with a computer controller herein disclosed.

Having described the preferred embodiment of this apparatus of the present system, the method of using this apparatus to practice the invention will now be discussed as summarized in the flowchart of FIG. 6. The operation of a surgical navigating system is generally well known and is described in PCT/US95/12894. In the preferred method of operation with the instrument 200 of the present invention, the position of the instrument tip 140 is determined by the user stepping on a foot pedal 116 to energize (300) the emitter array 150. The emitters 150 generate infrared signals to be picked up (310) by camera digitizer array 110, and triangulated (330) to determine the position of the cage 210 and thus tool tip 140. The relative position of the body part is determined in a similar manner (320), through the use of similar emitters 122 mounted on the reference frame 120 in mechanical communication with the body part. As is well known in this art and described in PCT/US95/12894, based upon the relative position of the body part, tool body 130 and the tool tip 140, after proper calibration of the tool 200 as is known in the art (such as by touching a known reference point) the computer would illustrate (340) a preoperative scan—such as the proper CAT scan slice—on the screen of monitor 106 which would indicate the position of the tool body 130 and tool tip 140.

When it becomes necessary or desirable to change the tool tip 140 by removing it (370) from tool body 130, for example by depressing or otherwise operating a chuck 260 on tool body 130, microswitch 160 is positioned so that it must automatically or necessarily be depressed or otherwise tripped (380) by the user to change the tool tip. Switch 160 communicates to the controller 108 that the tool tip 140 has been removed. In turn, the controller 108 communicates with the monitor 106 to indicate (400) a visual display of the fact of this removal. Alternatively, the controller 108 can communicate with an audio signal to a speaker system, or any other suitable alarm indication system, to indicate (400) the removal. Additionally, the controller 108 can communicate with the tool body 130 to disable (390) operation of the tool, such as disabling the drill, until proper tool interchange and subsequent recalibration is achieved.

Upon insertion (410) of a replacement or interchangeable tool tip 140, which may be of a different size or length, microswitch 160 will again be tripped or otherwise operated and communicate this act to controller 108. The user is thereby advised of the requirement to recalibrate (430) the location of tool tip 140, preferably by touching it to a known point on reference arc frame 120, or some other known point, such as a calibration divot. Alternatively, a fiber optic device can be provided for reading a bar code on the new tool tip 140, or the controller 108 can indicate a menu of alternative attachment tool tip configuration selections on monitor 106 for selection by the operator via key board or equivalent entry. Recalibration (430) of the tool tip location can be positively confirmed by means of a light emission from the LED array 150 (420) detected by the camera digitizer array 110 and triangulated (330) to determine the position of the tool tip 140. Once recalibrated in the surgical navigation system, the controller 108 can send a signal to tool body 130 to enable (350) further operation (i.e., conduct the medical procedure (360)), and can terminate audio and/or visual alarms. Additionally, controller 108 can indicate to the LEP 150, by flashing, that it is properly installed and relocated, providing a positive indication to the operator to continue the procedure.

It will be apparent to those skilled in the art that various modifications and variations can be made in the present invention and in construction of this surgical navigation system without departing from the scope or spirit of the invention. Other embodiments of the invention will be apparent to those skilled in the art from consideration of the specification and practice of he invention disclosed herein. It is intended that the specification and examples be considered as exemplary only.

What is claimed is:

1. A medical instrument with at least one electrically energizable energy emitter array thereon for use with a computer controlled surgical navigation system employing an energy-detecting digitizer array to track positions of the instrument in three dimensional space relative to a known reference point, said instrument comprising:

a tool body;

at least one instrument attachment removably coupled to said tool body, said at least one instrument attachment including at least one tool tip and at least one emitter coupled to said at least one instrument attachment;

an attachment member mountable about said instrument attachment and said tool body for removably coupling said at least one tool tip to said tool body;

at least one sensor positioned to be operated in response to said tool tip being changed by either coupling to or removal from said tool body;

a controller operatively connected to said sensor to detect when said sensor has been operated and said tool tip has been changed; and an indicator responsive to said controller for communicating to a user of said instrument that the tool tip of said instrument has been changed.

2. The instrument of claim 1, wherein said emitter is fixedly mounted to said instrument attachment for identifying a location of said instrument attachment.

3. The instrument of claim 1, wherein said sensor is an electrical switch.

4. The instrument of claim 3, wherein said controller, in response to the operation of said switch, can deactivate said instrument, and in response to recalibrating a location of said tool tip, can reactivate said instrument.

5. The instrument of claim 1, wherein said sensor is positioned to be operated in response to opening or closing of a chuck mounted on one end of said tool body.

6. The instrument of claim 1, wherein said indicator includes a visual display.

7. The instrument of claim 1, wherein said indicator includes an audible indication.

8. The instrument of claim 1, wherein said at least one emitter is rotatably mounted to said instrument attachment for use in identifying locations of said instrument attachment and said tool tip to said controller.

9. The instruction of claim 1, wherein said emitter array includes at least one passive reflective surface for reflecting signals to be tracked by the digitizer array.

10. The instrument of claim 2, wherein said emitter array includes at least one LED which can be activated by said controller upon recalibrating the location of said tool tip.

11. The instrument of claim 2, wherein said emitter comprises a passive reflective surface.

12. The instrument of claim 2, wherein said instrument attachment includes a clamp for clamping said instrument attachment to said tool body.

13. A method for monitoring a location of an instrument having at least one emitter array in three dimensional space relative to a known reference point for use in a medical procedure employing a surgical navigation system with a computer controller and a digitizer array, said method comprising:

coupling an instrument attachment to a tool body with an attachment member mountable about said instrument attachment and said tool body, said instrument attachment removably coupled to said tool body and including a tool tip and at least one emitter coupled to said instrument attachment for communication with the digitizer array;

operating a sensor mounted on said tool body in response to said coupling step, said sensor being in communication with the controller;

detecting the operation of said sensor by the controller; and delivering an indication to a user of the instrument upon coupling or uncoupling of said tool tip from said tool body that said tool tip requires recalibration.

14. The method of claim 13, further comprising the step of recalibrating the location of said tool tip by touching said tool tip to a known reference point.

15. The method of claim 13, further comprising the steps of disabling the instrument when said sensor has been operated and enabling the instrument when the location of said tool tip has been recalibrated.

16. The method of claim 13, wherein the coupling step includes the step of engaging said tool tip into a chuck mounted on said tool body.

17. The method of claim 13, further comprising the step of generating a display of the location of said tool tip.

18. The method of claim 13, further comprising the step of emitting a signal from an emitter attached to the instrument attachment disposed between said tool tip and said tool body, the signal being received by an apparatus representatively indicating that signal on a visual display.

19. The method of claim 13, further comprising the step of radiating a signal from a passive reflective surface attached to the instrument attachment disposed between said tool tip and said tool body, the signal being received by an apparatus representatively indicating that signal on a visual display.

20. The method of claim 13, further comprising the steps of communicating the recalibration of the tool tip to the controller and indicating the recalibration at a receptor mounted on the tool tip.

21. A system for use in performing surgical and medical procedures with an instrument or tool with a tool body and tool tip and a computer controlled surgical navigation system employing an energy detecting array to track positions of the instrument in three dimensional space relative to a known reference point, said system comprising:

a tool body;

an instrument attachment removably coupled to said tool body and including a tool tip and means for emitting coupled to said instrument attachment;

means for detecting location of said tool tip, said emitting means capable of communicating with said location detecting means;

means for coupling said instrument attachment, including said tool tip, with said tool body, said means for coupling mountable about said instrument attachment and said tool body;

means for detecting coupling or uncoupling of said tool tip from said tool body;

means for delivering an indication of coupling or uncoupling of said tool tip to a computer-controlled display; and means for recalibrating the location of said tool tip in response to the indication.

22. The system of claim 21, wherein the means for detecting coupling is located adjacent an interface between said tool body and said tool tip.

23. The system of claim 21, further comprising a means for deactivating the instrument upon detection of uncoupling and means for reactivating the instrument upon recalibrating the position of the tool tip.

24. The instrument of claim 1, wherein said tool tip is insertably attached to said tool body through said instrument attachment.

25. A medical instrument with at least one energizable energy emitter array thereon for use with a computer controlled surgical navigation system employing an energy-detecting digitizer array to track positions of the instrument in three dimensional space relative to a known reference point, said instrument comprising:

an elongated tool body having a distal end with a chuck positioned thereon;

an elongated, hollow cage configured to removably receive the tool body such that the chuck is positioned at a distal end of the cage, the cage including at least one emitter;

a tool attachment removably mounted to the distal end of the cage and surrounding the chuck, the tool attachment including a tool tip removably insertable into the chuck;

at least one sensor positioned at the distal end of the cage;

a removable, ring-like attachment member that encircles the tool attachment and chuck;

a controller operatively connected to said sensor to detect when said sensor has been operated and said tool tip has been changed; and an indicator responsive to said controller for communicating to a user of said instrument that the tool tip of said instrument has been changed, wherein the ring-like attachment member engages the tool attachment and chuck to secure the tool tip to the tool body and wherein the at least one sensor is activated during the engagement of the tool attachment and chuck to indicate coupling of the tool tip to said tool body.

26. The instrument of claim 25, wherein, when the ring-like member is removed, the tool tip is released from the tool body and the sensor is substantially simultaneously disengaged.

27. The instrument of claim 25, wherein the controller can deactivate the instrument in response to engagement of the sensor, and can reactivate the instrument in response to recalibrating location of the tool tip.

28. The instrument of claim 25, wherein the emitter is rotatable relative to the cage.

29. The instrument of claim 25, wherein the emitter array includes at least one reflective surface that reflects signals to be tracked by the digitizer array.

30. The instrument of claim 25, wherein the emitter array includes at least one LED which can be activated by the controller upon recalibrating location of the tool tip.

31. A medical instrument with at least one energizable energy emitter array thereon for use with a computer controlled surgical navigation system employing an energy-detecting digitizer array to track positions of the instrument in three dimensional space relative to a known reference point, said instrument comprising:

an elongated tool body;

an elongated, hollow cage configured to removably receive and encircle the tool body such that a distal end of the tool body is positioned at a distal end of the cage, the cage including a radially extending arm having at least one emitter thereon;

a tool attachment removably mounted to the distal end of the cage and surrounding the chuck, the tool attachment including a tool tip removably insertable into the chuck;

at least one sensor positioned at the distal end of the cage;

a removable, ring-like attachment member that encircles the tool attachment and chuck and is configured to secure the tool tip and engage the sensor;

a controller operatively connected to said sensor to detect when said sensor has been operated and said tool tip has been changed; and an indicator responsive to said controller for communicating to a user of said instrument that the tool tip of said instrument has been changed.

32. The instrument of claim 31, wherein the arm is rotatable relative to the cage.

33. The instrument of claim 31, wherein the emitter array includes at least one reflective surface that reflects signals to be tracked by the digitizer array.

34. The instrument of claim 31, wherein the emitter array includes at least one LED which can be activated by the controller upon recalibrating location of the tool tip.

35. The instrument of claim 31, wherein the attachment member releases the tool tip and disengages the sensor when removed from the tool attachment.

36. The instrument of claim 31, wherein the controller can deactivate the instrument in response to engagement of the sensor, and can reactivate the instrument in response to recalibrating location of the tool tip.

37. A method of monitoring a location of an instrument having at least one emitter array in three dimensional space relative to a known reference point for use in a medical procedure employing a surgical navigation system with a computer controller and a digitizer array, said method comprising:

removably inserting a tool body into a hollow cage such that a distal end of the tool body is positioned at a distal end of the cage;

sliding a ring-like attachment member over an instrument attachment, including a tool tip, and the distal end of the tool body to secure the tool tip to the tool body while substantially simultaneously engaging a sensor positioned at the distal end of the cage, the instrument attachment including at least one emitter coupled to said instrument attachment for communication with the digitizer array, and the sensor being in communication with the controller;

detecting engagement and disengagement of the sensor by the controller; and delivering, upon securing the tool tip to the tool body, an indication to a user of the instrument that the tool tip requires recalibration.

38. The method of claim 37, further comprising recalibrating location of the tool tip by touching the tool tip to a known reference point.

39. The method of claim 37, further comprising disabling the instrument when the sensor has been engaged and enabling the instrument when the location of the tool tip has been recalibrated.

40. The method of claim 37, wherein securing the tool tip to the tool body includes inserting the tool tip into a chuck mounted at the distal end of the tool body.

41. The method of claim 37, further comprising generating a display of location of the tool tip.

42. The method of claim 37, further comprising emitting a signal from the at least one emitter, the signal being received by an apparatus representatively indicating the signal on a visual display.

43. The method of claim 37, further comprising radiating a signal from the at least one emitter, the emitter being a reflective surface, and the signal being received by an apparatus representatively indicating the signal on a visual display.

44. The method of claim 37, further comprising communicating recalibration of the tool tip to the controller, and indicating the recalibration at a receptor mounted on the tool tip.

45. A medical instrument with at least one energizable energy tracker array thereon for use with a computer controlled surgical navigation system employing an energy-detecting digitizer array to track positions of the instrument in three dimensional space relative to a known reference point, said instrument comprising:
- an elongated tool body;
- an elongated, hollow cage configured to removably receive and encircle the tool body such that a distal end of the tool body is positioned at a distal end of the cage, the cage including a radially extending arm having at least one tracker thereon;
- a tool attachment removably mounted to the distal end of the cage and surrounding a chuck, the tool attachment including a tool tip removably insertable into the chuck;
- at least one sensor positioned at the distal end of the cage;
- a removable, ring-like attachment member that encircles the tool attachment and chuck and is configured to secure the tool tip and engage the sensor;
- a controller operatively connected to said sensor to detect when said sensor has been operated and said tool tip has been changed; and
- an indicator responsive to said controller for communicating to a user of said instrument that the tool tip of said instrument has been changed.

46. A medical instrument with at least one detectable tracker thereon for use with a computer controlled surgical navigation system configured to track positions of the instrument in three dimensional space relative to a known reference point, said instrument comprising:
- a tool body;
- at least one instrument attachment removably coupled to said tool body, said at least one instrument attachment including at least one tool tip and at least one tracker coupled to said at least one instrument attachment;
- an attachment member mountable about said instrument attachment and said tool body for removably coupling said at least one tool tip to said tool body;
- at least one sensor positioned to be operated in response to said tool tip being changed by either coupling to or removal from said tool body;
- a controller operatively connected to said sensor to detect when said sensor has been operated and said tool tip has been changed; and
- an indicator responsive to said controller for communicating to a user of said instrument that the tool tip of said instrument has been changed.

47. The instrument of claim 46, wherein the tracker is an emitter.

48. The instrument of claim 46, wherein the tracker is a light emitting diode (LED) emitter.

49. A medical instrument with at least one detectable tracker thereon for use with a computer controlled surgical navigation system configured to track positions of the instrument in three dimensional space relative to a known reference point, said instrument comprising:
- an elongated tool body;
- an elongated, hollow cage configured to removably receive and encircle the tool body such that a distal end of the tool body is positioned at a distal end of the cage, the cage including a radially extending arm having at least one tracker thereon;
- a tool attachment removably mounted to the distal end of the cage and surrounding a chuck, the tool attachment including a tool tip removably insertable into the chuck;
- at least one sensor positioned at the distal end of the cage;
- a removable, ring-like attachment member that encircles the tool attachment and chuck and is configured to secure the tool tip and engage the sensor;
- a controller operatively connected to said sensor to detect when said sensor has been operated and said tool tip has been changed; and
- an indicator responsive to said controller for communicating to a user of said instrument that the tool tip of said instrument has been changed.

50. The instrument of claim 49, wherein the tracker is an emitter.

51. The instrument of claim 49, wherein the tracker is a light emitting diode (LED) emitter.

\* \* \* \* \*

UNITED STATES PATENT AND TRADEMARK OFFICE
CERTIFICATE OF CORRECTION

PATENT NO.    : 6,434,507 B1                                                             Page 1 of 1
DATED         : August 13, 2002
INVENTOR(S)   : John B. Clayton et al.

It is certified that error appears in the above-identified patent and that said Letters Patent is hereby corrected as shown below:

<u>Title page,</u>
Item [56], References Cited, U.S. PATENT DOCUMENTS, insert
-- 5,987,349 4/97 Schullz --.

<u>Column 6,</u>
Line 26, delete "a".
Line 49, "means," should be -- means. --
Line 57, "270," should be -- 270. --

<u>Column 8,</u>
Line 44, "LEP" should be -- LED --.
Line 53, "he" should be -- the --.

Signed and Sealed this

Fifteenth Day of April, 2003

JAMES E. ROGAN
*Director of the United States Patent and Trademark Office*